| United States Patent [19] | [11] Patent Number: 4,615,771 |
|---|---|
| Zimmerman et al. | [45] Date of Patent: Oct. 7, 1986 |

[54] METHOD OF SEPARATING BIS-(2-AMINOETHYL)ETHER FROM N-(2-METHOXYETHYL)MORPHOLINE BY AZEOTROPIC DISTILLATION AND EXTRACTION

[75] Inventors: Robert L. Zimmerman, Austin; Roger G. Duranleau, Georgetown, both of Tex.

[73] Assignee: Texaco Inc., White Plains, N.Y.

[21] Appl. No.: 818,519

[22] Filed: Jan. 13, 1986

Related U.S. Application Data

[63] Continuation-in-part of Ser. No. 699,296, Feb. 7, 1985, Pat. No. 4,579,630.

[51] Int. Cl.$^4$ .................. B01D 3/36; C07D 265/32
[52] U.S. Cl. .................. 203/46; 203/43; 203/59; 203/63; 203/81; 544/106; 544/177; 564/479; 564/497
[58] Field of Search .......... 203/59, 63, 44, 43, 203/38, 46, 81; 544/106, 177; 564/479, 497, 508

[56] References Cited

U.S. PATENT DOCUMENTS

| 2,126,600 | 8/1938 | Andrews et al. | 203/59 |
|---|---|---|---|
| 2,651,606 | 9/1953 | Deahl et al. | 203/59 |
| 3,331,756 | 7/1967 | Currier et al. | 203/69 |
| 3,400,129 | 9/1968 | Cour et al. | 203/52 |
| 3,420,828 | 1/1969 | Mulbauer | 544/177 |
| 3,433,788 | 3/1969 | Somekh et al. | 203/59 |
| 4,399,307 | 8/1983 | Shioyama | 203/59 |
| 4,407,703 | 10/1983 | Featherstone | 203/43 |
| 4,482,433 | 11/1984 | Drake | 203/59 |

*Primary Examiner*—Wilbur Bascomb
*Attorney, Agent, or Firm*—Jack H. Park; Kenneth R. Priem; Richard A. Morgan

[57] ABSTRACT

A method for the separation of bis-(2-aminoethyl)ether from N-(2-methoxyethyl)morpholine via azeotropic distillation using an entrainer such as monoethanolamine is described. The N-(2-methoxyethyl)morpholine is selectively removed by the monoethanolamine. The N-(2-methoxyethyl)morpholine is then separated from the monoethanolamine by liquid-liquid extraction using a non polar hydrocarbon or aromatic extraction solvent and distillation.

The N-(2-methoxyethyl)morpholine-monoethanolamine stream previously had no economic use. The separation is now economically effected and the N-(2-methoxyethyl)morpholine used as a polyurethane catalyst.

12 Claims, No Drawings

METHOD OF SEPARATING BIS-(2-AMINOETHYL)ETHER FROM N-(2-METHOXYETHYL)MORPHOLINE BY AZEOTROPIC DISTILLATION AND EXTRACTION

CROSS-REFERENCE TO RELATED APPLICATIONS

This application is a continuation-in-part of Ser. No. 06/699,296 filed Feb. 7, 1985, and now U.S. Pat. No. 4,579,630.

BACKGROUND OF THE INVENTION

1. Field of the Invention

The invention relates to an amine separation method and more particularly relates to a method for the separation of bis-(2-aminoethyl)ether from N-(2-methoxyethyl)morpholine by means of azeotropic distillation followed by solvent extraction.

2. Description of Other Relevant Methods in the Field

Bis-(2-aminoethyl)ether (BAEE) and N-(2-methoxyethyl)morpholine (MEM) are co-products in the production of morpholine when diethylene glycol and ammonia are used as the reaction feed. These two co-products are very difficult to separate by conventional distillation because of their close boiling points. It would be advantageous to separate these two compounds because BAEE can be methylated to form beta-(N,N-dimethylaminoethyl) ether which is useful as catalyst in polyurethanes according to U.S. Pat. No. 3,330,782, incorporated by reference herein. And, MEM is a well known polyurethane foam catalyst.

Amines have been separated from other compounds according to some of the following techniques. U.S. Pat. No. 3,033,864 discloses the purification of pyrazines and piperazines by azeotropic distillation. In that patent, the objective was to remove unreacted alkanolamines by means of co-distillation agents comprising aliphatic hydrocarbons, aromatic hydrocarbons and nuclear chlorinated aromatic hydrocarbons having normal boiling points between about 130° C. and 200° C. Representative examples given were octane and higher aliphatic hydrocarbons, petroleum fraction mixtures, ethylcyclohexane, ethylbenzene, the xylenes, diethylbenzene, ethyltoluene, cumene and chlorobenzene.

A process for recovering piperazine from a mixture with triethylenediamine is described in U.S. Pat. No. 3,105,019. The inventors therein found that aliphatic hydrocarbons and especially saturated aliphatic hydrocarbons would be suitable azeotropic agents for the piperazine-triethylenediamine split if the boiling points were in the range from 110° C. to about 200° C., with particularly good results being obtained if the boiling point is within the range from about 140° C. to about 160° C. Specific compounds mentioned and tried were 3-methylheptane, 2-ethylhexene, 1,2-dimethylcyclohexane, meta-xylene, nonane, styrene, mesitylene, kerosene and 1-methylnaphthalene.

A method of recovering the major by-products from piperazine reaction residue is presented in U.S. Pat. No. 3,331,756. It was taught therein that hydrocarbons immiscible with diethylenetriamine and boiling within the range of about 175° C. to about 250° C. would be suitable entrainers for use in the separation of diethylenetriamine and aminoethylpiperazine. Two azeotropic agents mentioned were tetrapropylene and n-dodecane, with tetrapropylene being preferred because it gave a cleaner separation.

U.S.S.R. Pat. No. 472,122 teaches that diethylenetriamine and aminoethylpiperazine may be separated from reaction mixtures (especially those from the synthesis of a diamine and piperazine) by means of azeotropic rectification using a hydrocarbon mixture boiling at 160° C. to 174° C. yielding an azeotrope with DETA. The inventors found that the fractionation is simpler with n-decane than with dodecane or tetrapropylene.

The separation of an alkylene open chain polyamine from a piperazine compound may be accomplished by complexing the polyamine with a salt selected from the group consisting of sulfates and chlorides of copper, nickel, cobalt and zinc, according to the invention disclosed in U.S. Pat. No. 3,038,904. The complex compounds are extracted with substances such as chloroform or are allowed to precipitate. U.S. Pat. No. 3,400,129 reveals that 2-methyl triethylenediamine can be purified in a process which incorporates a two-solvent extraction step. One of the solvents is water and the other is an organic solvent for pyrazines, such as hexene, octene, nonene, benzene, toluene, xylenes, ethylbenzene, propylbenzene, n-hexane, n-heptane, isooctane, n-nonane, methylnonane, chlorobenzene, chlorotoluenes, diethylether, furan and alkylbenzonitriles. The method includes an azeotropic distillation step where 2-methylpiperazine is distilled and a step where the purified 2-methyl triethylenediamine is recovered.

Other, less desirable methods for separating amines have been devised. For example, U.S. Pat. No. 3,420,828 to Muhlbauer uses ethylene oxide to react with BAEE to permit MEM to be distilled. U.S. Pat. No. 3,417,141 to Feldman, et al. teaches the separation of monoamines from diamines having six or more carbon atoms via liquid-liquid extraction with a polar solvent and a non-polar solvent. U.S. Pat. No. 3,038,904 to Godfrey reveals the separation of polyamines from piperazine compounds via application of metal sulfates or metal chlorides.

U.S. Pat. No. 2,691,624 to Challis discloses a process for separating di-n-propylamine and tri-n-propylamine from a mixture containing di-n-propylamine, tri-n-propylamine, n-propanol and water by co-distilling with cyclohexane or benzene. The secondary amine content of an impure tertiary amine may be reduced by forming two organic phases based on the tertiary amine using hydrogen fluoride according to British Pat. No. 1,020,513 to Stevens, et al. Additionally, U.S.S.R. Pat. No. 472,122, as abstracted by Derwent, teaches the separation of diethylenetriamine and aminoethylpiperazine by azeotropic fractionation with hydrocarbons boiling at 160°–174° C. The separation of water soluble amines, such as morpholine, from their aqueous solutions may be accomplished by inert organic solvents miscible with the morpholine but not the water as taught by French Pat. No. 1,407,305. Further, Japanese Patent Document No. 55-127349 suggests simultaneous removal of water and picoline from primary arylamines by subjecting the mixture to distillation in the presence of toluene, according to the Derwent abstract.

In Advances in Chemistry Series No. 116: Azeotropic Data III, 1973, L. H. Horsley lists a number of binary azeotropic systems.

Non-polar hydrocarbons such as methane, butane, isopentane, etc. are used in the separation of primary amines and tertiary amines according to U.S. Pat. No.

4,552,957. These same non-polar hydrocarbons together with water are used in the extraction of the same close boiling amines, primary and tertiary, disclosed in U.S. Pat. No. 4,552,958.

SUMMARY OF THE INVENTION

The invention relates to a method for the separation of bis-(2-aminoethyl)ether from N-(2-methoxyethyl)-morpholine, by azeotropically distilling a mixture containing both compounds with a selective entrainer to remove the N-(2-methoxyethyl)morpholine with the entrainer. N-(2-methoxyethyl)morpholine is extracted from the entrainer with a non polar hydrocarbon or aromatic extraction solvent and recovered, optionally by conventional distillation.

N-(2-methoxyethyl)morpholine is used as a polyurethane catalyst. The unseparated N-(2-methoxyethylene)morpholine-entrainer mixture has no commercial use as stated in Ser. No. 06/699,296 filed Feb. 7, 1985, now U.S. Pat. No. 4,579,630.

DETAILED DESCRIPTION OF THE PREFERRED EMBODIMENTS

Bis-(2-aminoethyl)ether (BAEE) and N-(2-methoxyethyl)morpholine (MEM) are both by-products in the production of morpholine from diethylene glycol and ammonia. This method of producing morpholine is referred to in U.S. Pat. Nos. 2,412,209 and 3,151,112, incorporated herein by reference. However, BAEE and MEM are difficult to separate from each other by conventional distillation because they have close boiling points.

The method of the instant invention allows for separating these two co-products so that both may be used commercially. The method involves azeotropic distillation of the mixed co-product stream with monoethanolamine which selectively removes MEM from the mixture. Once the BAEE and the MEM have been separated, BAEE may be methylated and used most economically as polyurethane catalyst. The MEM has heretofore not been recovered from the monoethanolamine. The disposition of the MEM-monoethanolamine stream has been to burn it because there has been no economically feasible method for recovering the MEM in a useable form.

The addition of monoethanolamine (MEA) helps to entrain the MEM. Other compounds with structures similar to MEA, such as ethylenediamine, ethylene glycol, methyl ethanolamine, isopropanol amine and water, were ineffective entrainers for this purpose. MEM has all of the nitrogen valences occupied and is, therefore, relatively non-polar as compared with BAEE which has only one substituent on the nitrogen atom.

The monoethanolamine should be employed in excess quantities. Economic considerations for azeotropic distillation set an upper limit on the amount of entrainer which should be used. The azeotrope occurs at about 2:1 @ 1 atm. and excess entrainer makes for an easier separation. When the pressure is reduced to 50 mm Hg, entrainer in an amount down to about 1:1 produces good results. The best results attained in the laboratory @ 1 atm. were entrainer:tertiary amines weight ratios of 2:1 to 5:1. Generally, the monoethanolamine:tertiary amine weight proportion should be from 1:1 to 10:1, preferably 2:1 to 5:1, with processing considerations, plant design and economics setting the exact ratio.

Monoethanolamine is as stated the very most preferred entrainer for economic considerations. From purely technical considerations, an aminoalcohol boiling between 170° C. and 200° C. @ 1 atm. will do. Of these, preferable choices are 3-amino-1-propanol boiling at 184°–186° C. @ 1 atm. and 2-amino-1-propanol boiling at 173°–176° C. @ 1 atm. Criticality is demonstrated with isopropanolamine boiling at 159.9° C. @ 1 atm., for example, which entrains tertiary amine only when used in economically unsuitable excess.

The MEM is next extracted from the entrainer by liquid-liquid extraction with a non polar hydrocarbon or aromatic extraction solvent. The extraction solvent should be employed in excess over minimum quantities, although economic considerations for this extraction process will set an upper limit on the amount of solvents which can be used. The system may be dry. Generally, the preferred water content is 5 to 85 wt % based on the total weight of water, extraction solvent, MEM and extraneous hydrocarbon. In turn, the extraction solvent content is preferred to be 10 to 90 wt % based on the total weight of water, extraction solvent, MEM and extraneous hydrocarbon.

The process may be conducted at or near ambient temperatures. The method would be useful throughout temperature and pressure conditions from the freezing point of the MEM mixture to the approximate boiling point of the mixture. These extractive solvents may even be useful above the critical point of the mixture. Selectivity to the separation concentration would be dependent on temperature, but would not vary with the pressure.

The invention will be further illustrated by the following example.

EXAMPLE I

In a separatory funnel were placed 900 g of a mixture (2:1) of monoethanolamine and methoxyethylmorpholine and 300 g of cyclohexane. The separatory funnel was shaken and the phases allowed to separate. The lower layer, monoethanolamine phase, was drained off. This phase was washed with 300 g more of cyclohexane. The two cyclohexane phases were then combined. Gas chromatography showed that the cyclohexane phase contained only cyclohexane and methoxyethylmorpholine. No monoethanolamine was present. This phase was distilled to give pure methoxyethylmorpholine. The monoethanolamine phase did contain some cyclohexane, and methoxyethylmorpholine as well as monoethanolamine.

| | Gas Chromatogram | |
|---|---|---|
| Compound | Cyclohexane phase | Monoethanolamine phase |
| Cyclohexane | 69.5 area % | 1.8 area % |
| Monoethanolamine | 0 | 91.4 |
| Methoxyethylmorpholine | 31.5 | 6.8 |

EXAMPLE II

A. Example I was repeated with the addition of 300 grams water.

B. Example I was repeated with hexane substituted for cyclohexane.

C. Example I was repeated with toluene substituted for cyclohexane.

| Compounds | Gas Chromatograms | | | | | |
|---|---|---|---|---|---|---|
| | Example II-A | | Example II-B | | Example II-C | |
| | Cyclohexane | MEA | Hexane | MEA | Toluene | MEA |
| Hexane | — | — | 73.3 | 6.0 | — | — |
| Cyclohexane | 74 | 4.5 | — | — | — | — |
| Toluene | — | — | — | — | 69.4 | 4.7 |
| Water | — | 34.8 | — | — | — | 36.2 |
| Methoxyethylmorpholine | 26 | 7.8 | 26.7 | 8.2 | 30.3 | 3.4 |
| Monoethanolamine | — | 52.7 | — | 84.4 | — | 55.8 |

EXAMPLE III

Methoxyethylmorpholine can be isolated from the products of Example II by distillation.

The examples illustrate that MEM and BAEE may be separated by the MEA azeotropic distillation extraction technique. Although only batch equipment was used in these extractions, continuous or continuous countercurrent apparatus may be used also.

Many modifications may be made in the method of this invention by one skilled in the art without departing from the spirit and scope of the inventive method which is defined only by the appended claims. For example, in a continuous process, solvent recycle is envisioned.

What is claimed is:

1. A method for the separation of bis-(2-aminoethyl) ether from N-(2-methoxyethyl)morpholine comprising:
   a. azeotropically distilling a mixture comprising bis-(2-aminoethyl)ether and N-(2-methoxyethyl)morpholine with an entrainer to selectively remove the N-(2-methoxyethyl)morpholine with the entrainer, and
   b. extracting the N-(2-methoxyethyl)morpholine from the entrainer by means of liquid-liquid extraction using a non polar hydrocarbon or aromatic extraction solvent.

2. The method of claim 1 which additionally comprises:
   c. distilling N-(2-methoxyethyl)morpholine from the extraction solvent.

3. The method of claim 1 wherein in step b. there is 5 to 85 wt % water present.

4. The method of claim 1 wherein the amount of N-(2-methoxyethyl)morpholine in step b. is 10 to 90 wt %.

5. A method for the separation of bis-(2-aminoethyl) ether from N-(2-methoxyethyl)morpholine comprising:
   a. azeotropically distilling a mixture comprising bis-(2-aminoethyl)ether and N-(2-methoxyethyl)morpholine with an entrainer selected from the group consisting of monoethanolamine, 3-amino-1-propanol and 2-amino-1-propanol to selectively remove the N-(2-methoxyethyl)morpholine with the entrainer, and
   b. extracting the N-(2-methoxyethyl)morpholine from the entrainer by means of liquid-liquid extraction using an extraction solvent selected from the group consisting of hexane, heptane, cyclohexane, benzene, toluene and xylene.

6. The method of claim 1 which additionally comprises:
   c. distilling N-(2-methoxyethyl)morpholine from the extraction solvent.

7. The method of claim 1 wherein in step b. there is 5 to 85 wt % water present.

8. The method of claim 1 wherein the amount of N-(2-methoxyethyl)morpholine in step b. is 10 to 90 wt %.

9. A method for the separation of bis-(2-aminoethyl) ether from N-(2-methoxyethyl)morpholine comprising:
   a. azeotropically distilling a mixture comprising bis-(2-aminoethyl)ether and N-(2-methoxyethyl)morpholine with monoethanolamine to selectively remove the N-(2-methoxyethyl) morpholine with the monoethanolamine, and
   b. extracting the N-(2-methoxyethyl)morpholine from the monoethanolamine with an extraction solvent selected from the group consisting of hexane, cyclohexane and toluene.

10. The method of claim 4 which additionally comprises:
    c. distilling N-(2-methoxyethyl)morpholine from the extraction solvent.

11. The method of claim 1 wherein in step b. there is 5 to 85 wt % water present.

12. The method of claim 1 wherein the amount of N-(2-methoxyethyl)morpholine in step b. is 10 to 90 wt %.

* * * * *